(12) United States Patent
Patel et al.

(10) Patent No.: US 7,837,844 B2
(45) Date of Patent: Nov. 23, 2010

(54) INTERDIGITATED CHEMICAL SENSORS, AND METHODS OF MAKING AND USING THE SAME

(75) Inventors: Sanjay V. Patel, San Diego, CA (US); Todd E. Mlsna, Carlsbad, CA (US); Erno Klaasen, Los Altos, CA (US)

(73) Assignee: Seacoast Science, Inc., Carlsbad, CA (US)

( * ) Notice: Subject to any disclaimer, the term of this patent is extended or adjusted under 35 U.S.C. 154(b) by 1557 days.

(21) Appl. No.: 11/115,911

(22) Filed: Apr. 26, 2005

(65) Prior Publication Data

US 2006/0237310 A1  Oct. 26, 2006

(51) Int. Cl.
*G01N 27/327* (2006.01)
*G01N 27/30* (2006.01)

(52) U.S. Cl. .................................. 204/403.01; 204/400
(58) Field of Classification Search ......... 204/400–416; 205/777.5, 778, 792
See application file for complete search history.

(56) References Cited

U.S. PATENT DOCUMENTS

| | | | |
|---|---|---|---|
| 5,164,319 A * | 11/1992 | Hafeman et al. ......... | 435/287.1 |
| 5,312,762 A | 5/1994 | Guiseppi-Elie | |
| 5,391,272 A * | 2/1995 | O'Daly et al. ........... | 205/777.5 |
| 5,682,788 A * | 11/1997 | Netzer ........................ | 73/73 |
| 5,880,552 A | 3/1999 | McGill et al. | |
| 6,535,822 B2 | 3/2003 | Mansky et al. | |

FOREIGN PATENT DOCUMENTS

| WO | WO 93/03355 A1 * | 2/1993 |
|---|---|---|
| WO | WO 95/32422 A1 * | 11/1995 |
| WO | WO 98/29740 A1 * | 7/1998 |

* cited by examiner

*Primary Examiner*—Alex Noguerola
(74) *Attorney, Agent, or Firm*—BioTechnology Law Group; Daniel M. Chambers

(57) ABSTRACT

The present invention relates to the field of chemical detection. More specifically, the invention provides devices that can detect various target analytes (e.g., chemicals and/or biological materials) present in an environment by adsorption or absorption of the target analyte(s) to or in a chemical sensing material such that an electrical parameter (e.g., capacitance, resistance, etc.) of the chemical sensing material is altered in a manner detectable by circuitry associated with the sensing electrode pair coated with the chemical sensing material. Here, the sensing electrode pair(s) of the devices of the invention are suspended over an inert substrate via one or more posts used to space the electrodes from the substrate.

16 Claims, 7 Drawing Sheets
(7 of 7 Drawing Sheet(s) Filed in Color)

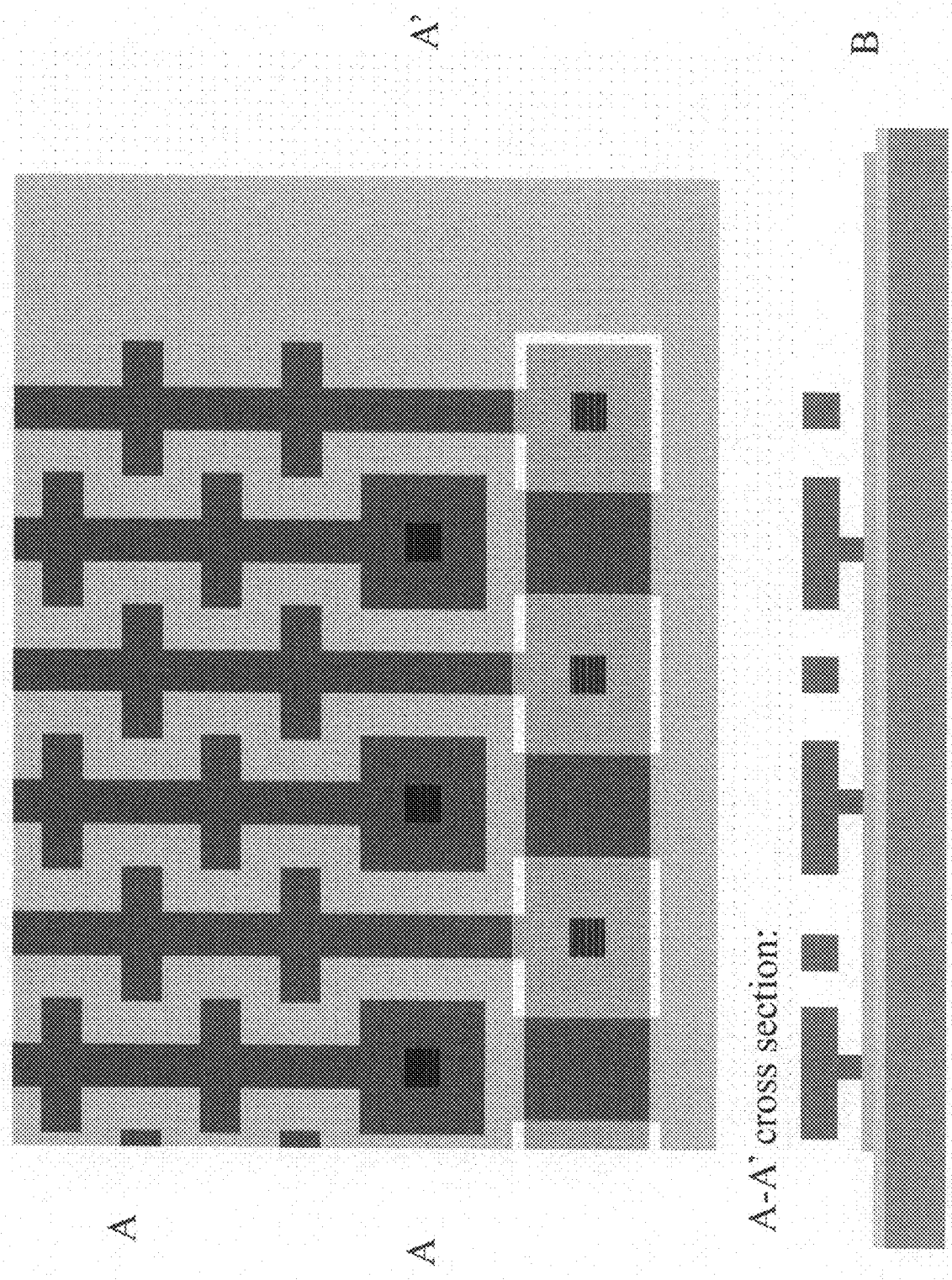

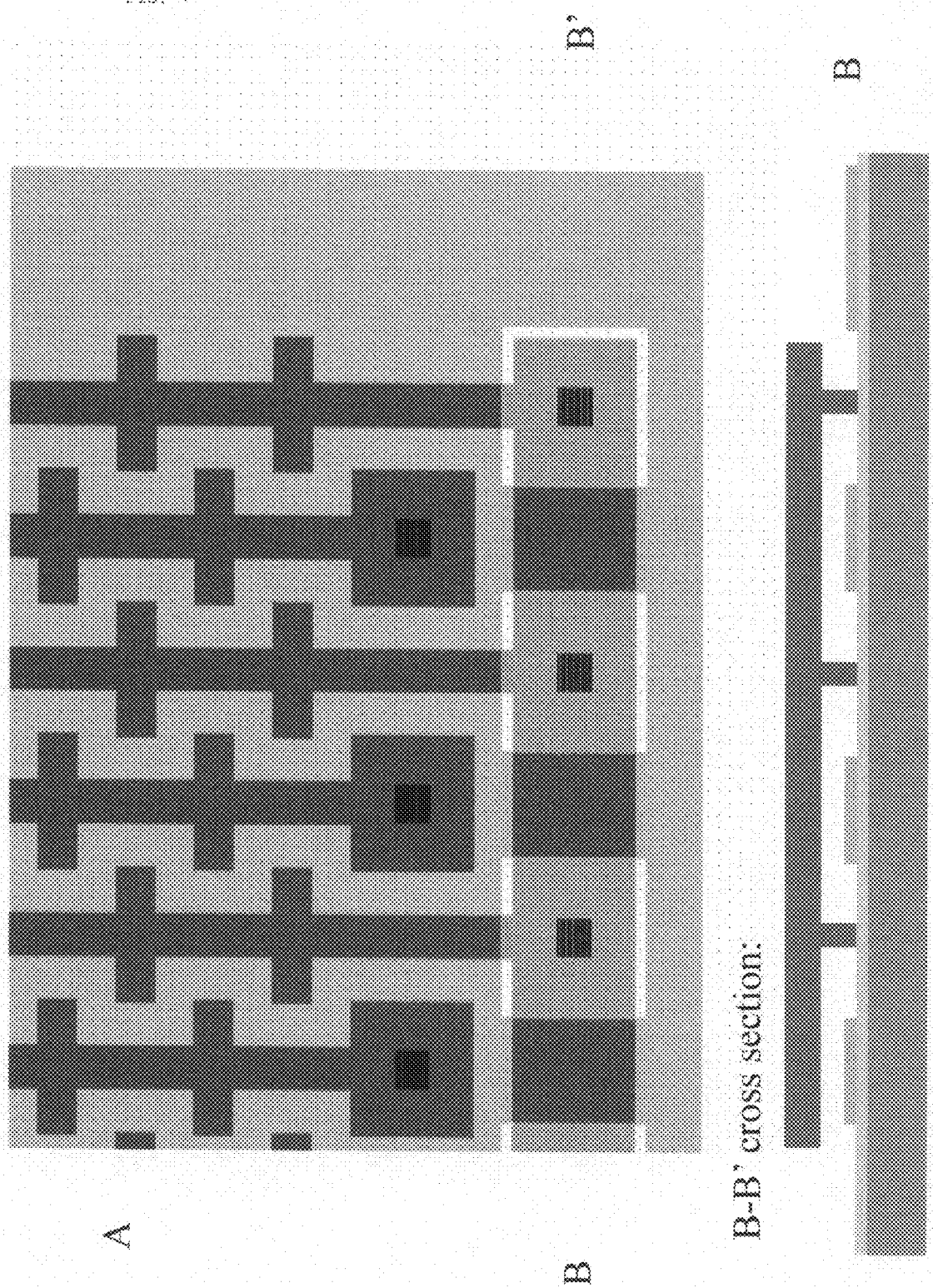

INTERDIGITATED CHEMICAL SENSORS, AND METHODS OF MAKING AND USING THE SAME

FIELD OF THE INVENTION

This invention relates generally to the field of chemical detection and environmental monitoring. More specifically, the invention concerns devices that can detect one or more chemicals and/or biological materials in an environment as a result of their adsorption by chemical sensing materials in the device, which adsorption or absorption alters a detectable electrical property of one or more electrode pairs in a circuit disposed in the device. In general, such sensors employ multiple pairs of interdigitated electrodes coated with at least one chemical sensing material, which electrode pair(s) is(are) suspended over an inert substrate, wherein an electrical parameter of an electrode pair, for example, capacitance, can be monitored and a change detected by circuitry in electrical communication with the electrode pair. Detected changes can then be analyzed to determine whether one or more particular chemicals or biological materials are present in the environment being monitored.

BACKGROUND OF THE INVENTION

1. Introduction.

The following description includes information that may be useful in understanding the present invention. It is not an admission that any such information is prior art, or relevant, to the presently claimed inventions, or that any publication specifically or implicitly referenced is prior art.

2. Background.

The ability to detect chemicals or biological materials in an environment is critically important in many contexts. For example, the detection of potential toxic chemicals in a home, place of business, industrial facility, or surrounding communities can prevent deaths, injuries, health problems in the event of accidents, fires, etc. The detection of unwanted chemicals or poisons in drinking water can alert users of the need to filter, purify, or treat the water before using to avoid adverse health consequences. It can also alert the water supplier of possible problems at the source or in the distribution system. Similarly, the detection of potentially harmful chemicals in lakes and other bodies of water can alert authorities to provide warnings to avoid consumption of fish and other fauna taken from the contaminated water source.

Further, the detection of chemicals and biological materials associated with explosives and chemical and biological warfare agents may be crucial in preventing acts of terrorism. Early detection of tell tale chemicals or biological materials can provide the opportunity to warn the public and, if warranted, allow evacuation of at risk areas and populations.

The accurate detection of certain chemicals is also important in many industrial settings. For example, many products and components, such as computer chips and certain medical devices, must be manufactured in environments free from contaminants. The ability to detect contaminants in such environments can improve product quality, reduce losses attributable to fouled products, etc.

Moreover, the detection of certain chemicals and molecules in biological fluids is important for both diagnostic and therapeutic reasons.

Conventional sensors typically have employed sensor arrays that use heated metal oxide thin film resistors, polymer sorption layers on the surfaces of acoustic wave resonators, arrays of electrochemical detectors, and conductive polymers to detect specific target analytes in various fluids, including those in vapors, gases, and liquids. Clearly, however, a need still exists for alternative sensing technologies, particularly those that enable fast, inexpensive, efficient, and sensitive detection of one, several, or many different chemical and/or biological entities.

3. Definitions.

When used in this specification, the following terms will be defined as provided below unless otherwise stated. All other terminology used herein will be defined with respect to its usage in the particular art to which it pertains unless otherwise noted.

A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that (1) preserves their validity and (2) provides the broadest reasonable interpretation under the circumstances.

A "plurality" means more than one.

The term "species" is used in various contexts, e.g., a particular compound species and cells from a particular species (e.g., mouse, human, etc.). In the context of compounds, the term refers to a population of chemically indistinct molecules of the sort referred to. For example, a "small molecule species" is a population of small molecules identified by the same chemical formula.

SUMMARY OF THE INVENTION

The object of this invention is to provide a new, patentable class of sensors that can be used to detect various chemicals and biological materials. At its core, the invention employs one or more sensing electrode pairs. The sensing electrode pair(s) each comprise a pair of spaced sensing electrodes elevated or suspended above a substrate (preferably made of a chemically inert material) by one or more posts anchored directly or indirectly to the upper surface of the substrate, i.e., that surface that faces the drive and sense electrodes of each electrode pair. The drive and sense electrodes of each electrode pair are in electrical communication, and at least some, and preferably all, of each member of an electrode pair is coated with a chemical sensing material that is responsive to at least one, and frequently several or many, target analyte species, albeit to different extents. Upon adsorption or absorption of the target analyte by the chemical sensing material, an electrical parameter, for example, capacitance, current, resistance, or voltage, between the drive and sense electrodes of a sensing electrode pair changes, which change can be detected by circuitry in electrical communication with the sensing electrode pair. The resulting changes can then be analyzed to determine whether one or more particular target analytes are present in the environment being monitored. In certain preferred embodiments, a shield layer is disposed in or on the upper surface of the substrate before or after the posts for supporting the drive and sense electrodes are assembled on the substrate. Such a shield reduces stray capacitance through the substrate, thereby further increasing the sensitivity and the response time of the sensor. The shield layer may be continuous, in that it covers the surface the substrate (although posts may protrude through it if laid down all or in part before application of the shield layer) or, preferably, it may be laid down only on certain portions of the substrate. Particularly preferred are embodiments wherein a shield layer is not applied to the upper surface of the substrate substantially in the regions directly below the sense electrodes.

In general, the sensing electrode pairs are part of a chemical sensor. Two or more electrode pairs are often employed as part of an array of electrode pairs. As such, the electrode pairs that form part of an array tend to be powered simultaneously, although in some embodiments, switches or other circuitry can be used, for example, to provide for powering fewer than all of the electrode pairs of a given array at a particular time, and/or analyzing signals from fewer than all of the electrode pairs of a given array. In addition to the sensing electrode pairs, the chemical sensor also comprises a power supply (e.g., as may be provided by a battery) and circuitry electronically connected to the sensing electrode pairs (e.g., one or more amplifiers, analog-to-digital converters, temperature (or one or more other environmental parameters) compensating devices, one or more communication buses, one or more microprocessors and associated memory devices, etc.) that allows for the analysis of the changes that occur in the electrical parameter(s) being monitored between the various sensing electrode pairs.

When the chemical sensing material coating at least a portion of an electrode pair interacts with a target analyte, the result is an alteration in the electrical field between the drive and sense electrodes of a sensing electrode pair when energized. For any given sensor, the nature and extent of the alteration depends upon the type and concentration of the target analyte that interacts with the chemical sensing material coating at least a portion of the electrode pair. By deploying a plurality of different sensing electrode pairs coated with different chemical sensing materials in a given sensor, a wide variety of different target analytes (i.e., particular chemicals and/or biological materials to be sensed) can be detected in an environment using a single chemical sensor according to the invention.

In preferred embodiments, chemical sensors according to the invention include not only power supplies (typically provided by one or more batteries), but also a microprocessor configured to control the energizing of the sensing electrode pairs and analyze data from circuitry configured to detect changes in one or more electrical parameters of an energized sensing electrode pair, analog-to-digital converters, memory devices for storing data derived from the sense electrode circuits, as well as data and/or software for operating the sensor and for comparing results from the sense electrode circuits with data patterns representative of particular chemicals or biological materials, components that provide data logging and/or one- or two-way telemetry capability, etc.

The use of posts or other electrode-supporting structures to raise the drive and sense electrodes of an electrode pair off of the surface of the substrate allows a larger fraction of the electric field generated by the electrode pair to pass through the chemical sensing material instead of through the inert substrate, thereby increasing the portion of the resulting electric field available for sensing. Thus, the present invention provides for more sensitive detection of perturbations of that electrical field by a target analyte interacting with the chemical sensing material than would occur if the electrodes were not suspended above the facing surface of the substrate. Also, such elevated configurations provide for faster sensor response times by providing enhanced (e.g., faster, due to a relative increase in sensing material surface area exposed to the environment to be sensed) access of a target analyte to the chemical sensing material, by allowing target analyte-containing fluid to access the chemical sensing material coating the electrodes from all sides. The prior art sensors, which sat directly upon the substrate, blocked access to any chemical sensing material on the side of the electrode that contacted the substrate, and no sensing capacity could provided by the surface of the sensor in contact with the surface of the substrate on which it was disposed. As will be appreciated, faster vapor access results in faster sensor response time.

A related aspect of the invention concerns methods for making the sensing electrode pairs of the invention. Particularly preferred are techniques used in MEMS (micro-electromechanical systems) production, in which processes developed for the microfabrication of integrated circuits on common substrates (e.g., silicon substrates) are adapted for the integration of mechanical elements, sensors, actuators, and other electronics as well.

Still another aspect of the invention concerns methods of detecting one or more target analytes in a fluid through the use of one or more chemical sensors according to the invention, alone or in conjunction with other devices, for example, video and other security equipment. Such methods provide the capacity for the environmental monitoring and detection of target analytes including, without limitation, toxic or hazardous volatile organic chemicals, chemicals associated with the manufacture and/or presence of elicit drugs (e.g., heroin, marijuana, cocaine, methamphetamine, etc.) and explosives, environmental toxins (e.g., radon; heavy metals such as lead and mercury; etc.), combustion products (e.g., carbon dioxide, carbon monoxide, nitric oxides, etc.), chemical warfare agents (e.g., organophosphates such soman and sarin), pesticides, and biological materials, including bacteria (e.g., anthrax and anthrax spores), viruses, nucleic acid molecules, and proteins.

Other features and advantages of the invention will be apparent from the following brief description of the figures, detailed description, and appended claims.

BRIEF DESCRIPTION OF THE DRAWINGS

This patent or patent application publication contains at least one figure executed in color. Copies of this patent or patent application publication with color drawing(s) will be provided upon request and payment of the necessary fee. As those in the art will appreciate, the data and information represented in the attached figures is representative only and do not depict the full scope of the invention.

FIGS. 6 and 7, panels A and B, show cross-sections taken through the sensor array depicted in FIG. 5, panel B, in the planes A-A' and B-B', respectively. As shown in these cross sections, the shield layer (4) under the sense and drive electrodes depicted in FIG. 6, panel B, is continuous, whereas in the region of the sensor depicted in FIG. 7, panel B, the shield layer in not continuous.

Figure 1:
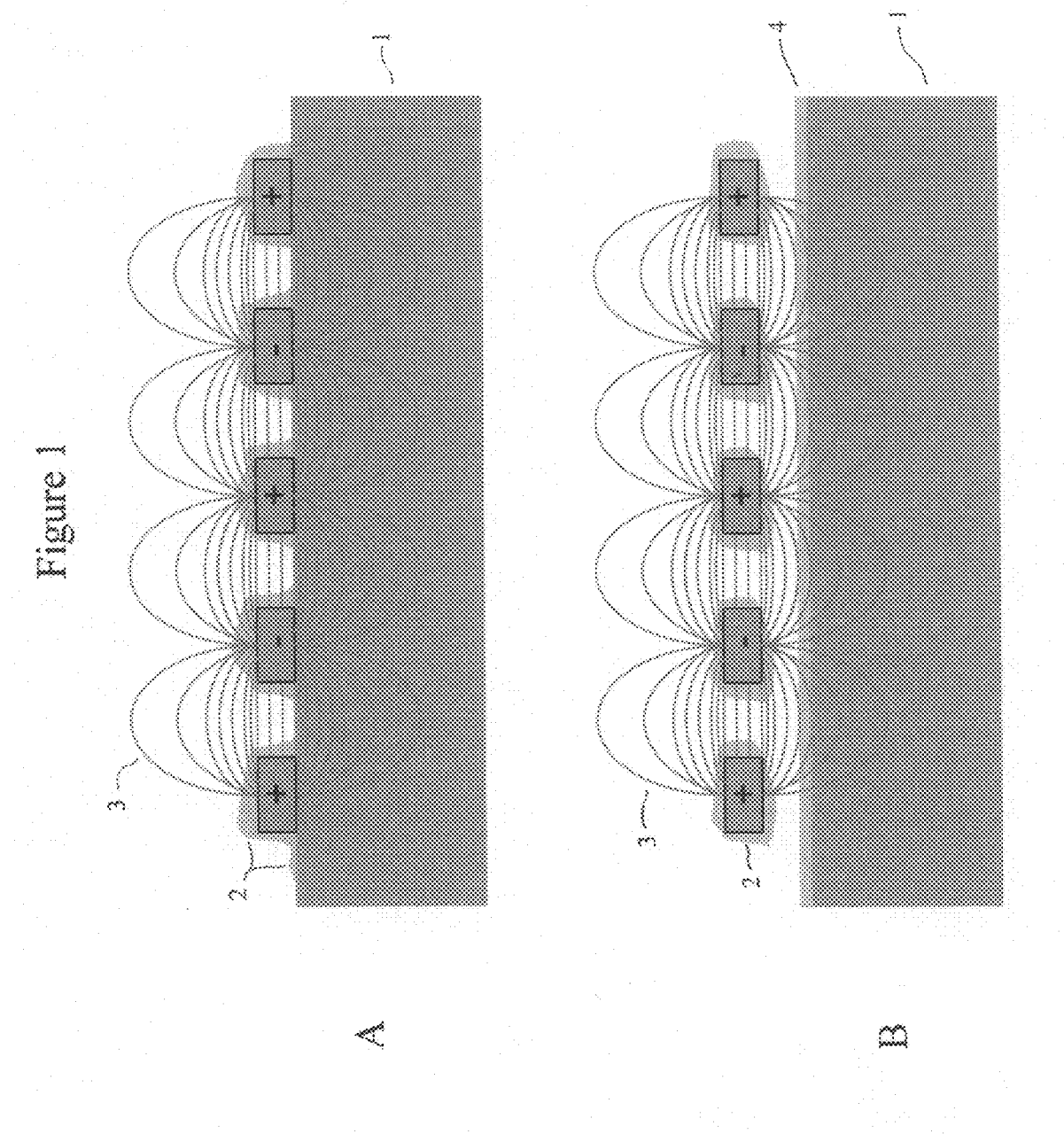
FIG. 1, panel A, depicts a conventional configuration of sensing electrode pairs, wherein each member of the pair (designated by either a "+" for a drive electrode or "−" for a sense electrode) is disposed directly on the upper surface of an inert substrate (1). Panel B depicts three sensing electrode pairs according to the present invention, wherein the drive ("+") and sense ("−") electrodes are suspended above the upper surface of the substrate (1), upon which a shield layer (4) has also been applied. In the Figure, sensing material (2) coats the surfaces of the electrodes not in contact with the substrate (1). Electric field lines (3) are depicted in red. As will be appreciated, in preferred embodiments the sensing materials (2) used to coat the various electrode pairs are different materials. Also, while the electrodes depicted in this Figure (and the other FIGS. 2-7) are depicted as being rectangular or square in cross section, any other suitable geometry may also be employed, although in embodiments that employ MEMS fabrication techniques in the manufacture of electrodes and sensor arrays, square or substantially rectangular cross section profiles are preferred.

As those in the art will appreciate, the following description describes certain preferred embodiments of the invention in detail, and is thus only representative and does not depict the actual scope of the invention. Before describing the present invention in detail, it is understood that the invention is not limited to the particular sensors and methods described, as these may vary. It is also to be understood that the terminology used herein is for the purpose of describing particular embodiments only, and is not intended to limit the scope of the invention defined by the appended claims.

DETAILED DESCRIPTION OF THE INVENTION

In one aspect, the present invention provides a sensor comprising at least one elevated sensing electrode pair that comprises a pair of spaced electrodes, wherein one of said pair is a drive electrode and the other of said pair is a sense electrode, and wherein the electrodes are coated, preferably over their length, with a chemical sensing material that is responsive to a target analyte. In a given sensor, each electrode is elevated above the substrate of the sensor by at least one post or anchor that spans from an upper surface of the substrate (or one or more intervening layers disposed on the substrate's upper surface) to a lower surface of the electrode. Preferably, the anchors that support and elevate the electrodes, particularly the sense electrodes, are not continuous, in that at least some portion of the surface area of the underside of the electrode that faces the substrate (or the uppermost surface of the shield layer disposed on the upper surface of the substrate) is not connected to an anchor. The electrode pair(s) of the sensor comprises the sensing portion of an operative electrical circuit in which at least one electrical parameter can be measured. As will be appreciated, the coated sensing electrode pair is useful in identifying target analytes present in a fluid, i.e., liquid, a vapor, or a gas.

The substrate in the sensing electrode pair of this invention can be made up of any solid conductive or non-conductive material, as long as the material can withstand the environment in which the sensing electrode pair(s) of the sensor will be used (the substrate must be chemically inert). Combinations of different materials, either as different layers or as a mixture, may also be used to make up the substrate. Examples of conductive materials that may be used to make the substrate utilized in this invention include, but are not limited to, metals and polycrystalline silicon. Examples of nonconductive materials that may be used to make the substrate (or a portion thereof, for example, an upper insulating portion to be disposed between a polycrystalline silicon lower layer and a shield layer underlying anchors and electrodes) include, but are not limited to, $SiO_2$, $Si_3N_4$, $Al_2O_3$, glass, ceramic, any insulator or any semiconductor. In a preferred embodiment, the insulating substrate is $Si_3N_4$.

The electrodes in the electrode pair of this invention are each independently made from one or more conductive materials. When an electrode of this invention is made up of multiple conductive materials, individual materials may be layered on top of one another to build up the electrode, or multiple materials may be mixed together prior to formulating the electrode. The electrodes of this invention may also be fabricated by a combination of these techniques. For example, a layering technique may be employed, wherein each layer independently consists of either a single material or a mixture of materials. Preferably, each electrode comprises the same materials and is fabricated in the same way.

Examples of conductive materials that can be used to make the electrodes of this invention include, but are not limited to, organic materials, inorganic materials, metallic, alloy, ceramic, polymer, non-metallic, ceramic-ceramic composite, ceramic-polymer composite, ceramic-metal composite, metal-polymer composite, polymer-polymer composite, metal-metal composite, or a combination of one or more of these. Preferably, the electrode is composed of a material selected from polycrystalline silicon, gold, aluminum, platinum, silver or a combination thereof.

The electrodes in the electrode pair of this invention should be spaced apart from one another and not in physical contact with one another. The drive electrode and the sense electrode are each part of the same circuit. The spacing between electrodes can range from a lower bound dictated by the manufacturing limitations in defining the electrode features to an upper bound of tens of microns. If tall electrodes are used, wider spacing between the electrodes can be adopted. In a preferred embodiment, the spacing between the electrodes is 3.5 µm.

The posts or anchors that elevate the electrodes of a sensing electrode pair of this invention above the substrate are preferably fabricated from a non-conductive material or combination of non-conductive materials. Any non-conductive material known in the art may be employed. In an alternate embodiment, these posts can include a conductive material if the point at which they contact the substrate is nonconductive. In a preferred embodiment, the posts are composed of a non-conductive material selected from $SiO_2$ or $Si_3N_4$. The posts may be continuous (in which event only a single "post is used") or two or more separated anchors can be used to elevate a given electrode. Moreover, the anchor may extend to cover the width of the electrode surface with which it is connected. Alternatively, a given anchor may be narrower in width than the electrode it elevates above the substrate. The particular anchor configuration (i.e., number, shape, size (e.g., height, width, and depth, if a regular geometric shape is used) employed in a given application is left to the discretion of the ordinarily skilled artisan.

As will be appreciated, the function of the posts is to elevate the electrodes of an electrode pair off of the surface of the substrate. This reduces the amount of the electric field (as may be represented by electrical field lines) that passes through or otherwise extends into the substrate when an electrical field is generated between the two members of the electrode pair. As shown in FIG. 1A, a conventional electrode-directly-on-substrate has a planar electrode structure wherein each electrode member of each electrode pair is affixed directly on the substrate. Such a configuration results in almost half of the electric field generated between the electrodes to travel through the substrate. In contrast, when the electrodes are raised off of the substrate surface, as in the present invention, a smaller portion of the electric field travels through the substrate (FIG. 1B). The height of the posts is preferably about 0.5 to about 10 µm. The height of the posts is ideally at least several times greater than the spacing between the electrodes of a given electrode pair.

According to a preferred embodiment, a plurality of posts are employed to elevate the electrode pair off of the surface of the substrate. The choice of utilizing one or a plurality of posts is dependent upon the length of the electrode and the need to support the suspension of the electrode. In a more preferred embodiment, the length of each member of the electrode pair is about 650 microns (i.e., micrometers, or "µm") and each electrode is supported by posts at both ends and additional posts spaced about every 75-100 µm.

The posts span a portion of the upper surface of the substrate and a portion of the lower surface on the electrode. In one preferred embodiment, the substrate comprises an uppermost shield layer of conductive material. This shield layer is employed to reduce stray capacitance (i.e., "fringing" capacitance) through the substrate when the shield layer is connected to a fixed voltage source, a ground, or one of the electrode pair members. Stray capacitance decreases the sensitivity of detection of a change in an electrical parameter of the sensing electrode pair. The shield layer can be made of any electrically conductive material, such as a metal or doped semiconductor.

The shield layer may be continuous and thus cover the entire substrate surface or it may comprise apertures, gaps, furrows, or other openings that leave portions of the substrate uncovered by shield layer material. Openings in the shield layer can be used to provide a location for support posts to mechanically connect the electrodes to the substrate. In an alternate embodiment, the shield layer can be embedded in the substrate.

When the substrate of a sensor according to the invention additionally comprises an uppermost shield layer, any post extending from a lower surface of the drive electrode is affixed to the shield layer. Any post extending from the lower surface of the sense electrode may be affixed to either the shield layer or to the substrate material. Preferably, the shield layer is not a continuous layer and is absent in a least the portion of the area underneath a sense electrode where a post is attached. Preferably, the openings in the shield layer are as small as possible, given the fabrication limits of the method used to produce the sensor array. Ideally, an opening in the shield layer is just large enough to allow an anchor to span between the substrate and the electrode above and to prevent electrical shorting between the post and the shield layer. This allows a post extending from the sense electrode to be affixed directly to the substrate material. The width of the area lacking shield layer material is most preferably equal to the width of the sense electrode.

Figure 2:
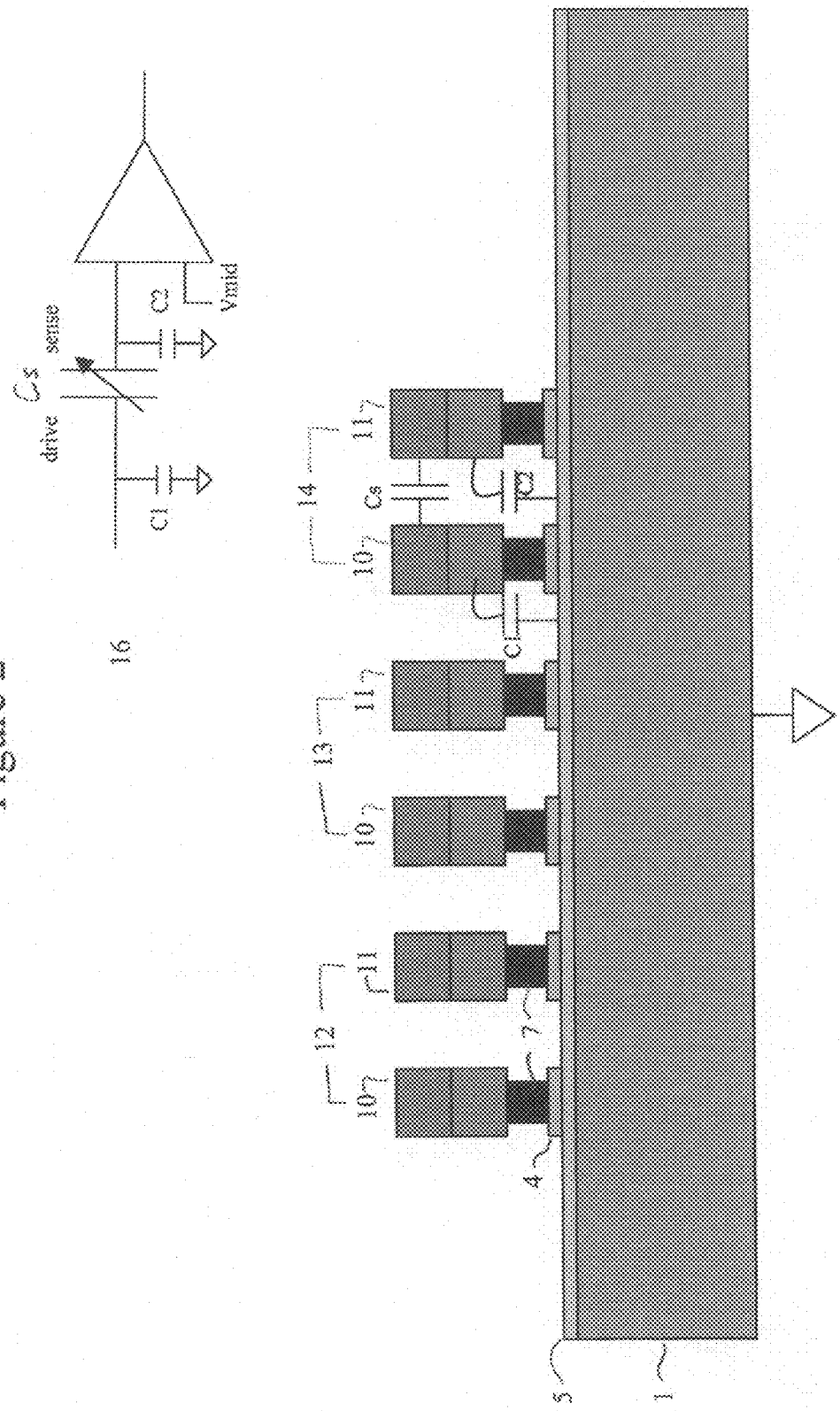
FIG. 2 depicts a preferred embodiment wherein three rigid sensing electrode pairs (12, 13, and 14), each containing a drive (10) and sense (11) electrode elevated above the surface of the substrate (1) on anchors (7), each of which anchor/electrode structures is affixed to a shield layer (4) disposed on the upper surface of the substrate, preferably on the upper surface of an insulating layer (5) disposed on the substrate (1) between the substrate and the shield layer (4). Also shown is the sensed capacitance (Cs) between one electrode pair, as well as two fringing capacitances, C1 and C2, that are not sensed in the illustrated embodiment, fringing capacitances reduce the effective capacitance (Cs). The inset shows a circuit (16) illustrating this embodiment. Chemical sensing material is not shown in this illustration.
Figure 3:
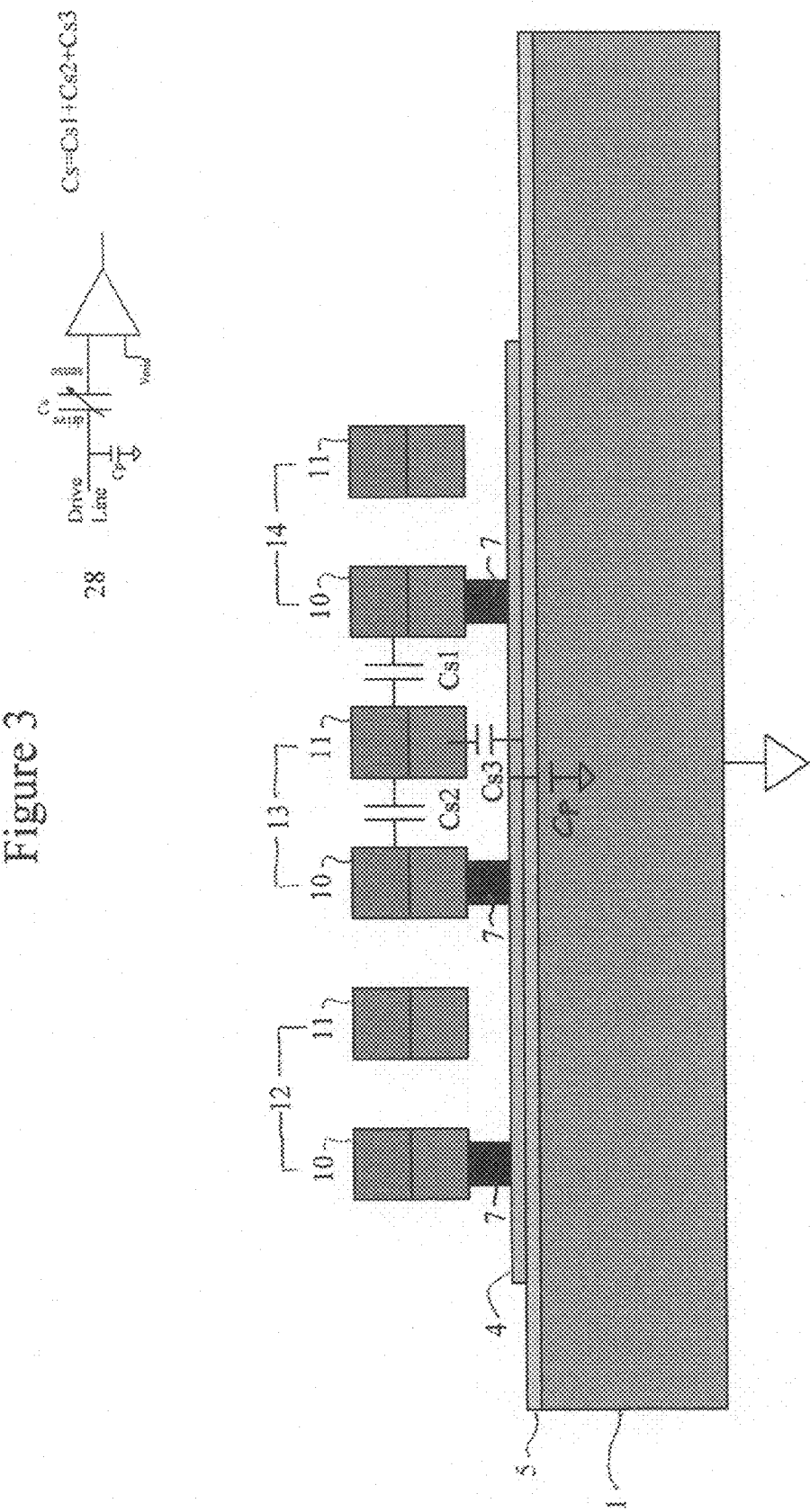
FIG. 3 depicts a preferred embodiment wherein the drive electrode (10) of each sensing electrode pair (12, 13, and 14) is affixed by a post (7) to a confluent shield layer (4) on top of an insulating layer (5) disposed on the upper surface of the substrate (1). In the illustrated embodiment, each sense electrode (11) is suspended above the shield layers. Capacitances between a sense and two drive electrodes, Cs1 and Cs2, between the sense electrode and the shield layer (Cs3), and the parasitic capacitance (Cp) of the substrate, are also illustrated. The inset shows a circuit (28) illustrating this embodiment, wherein the total sensing capacitance (Cs) is the sum of sensing capacitances Cs1, Cs2, and Cs3. Losses due parasitic capacitance (Cp) are also illustrated. Chemical sensing material is not shown in this illustration. In the illustrated embodiment, the spacing between the sense (11) and drive electrodes is 3.5 µm, as is the cross-sectional width of the each sense and drive electrodes, whereas the electrodes are elevated above the shield layer (4) by 2 µm.

As shown in FIG. 2, a capacitance is created between the raised electrodes and the substrate (C1 and C2) causing some effective capacitance between the drive and the sense electrode (Cs) to be lost. The deposition of a shield layer (poly0) on the upper surface of the substrate and the affixing of the posts to that shield layer eliminates C1 and C2. However, the presence of the shield layer underneath the suspended sense electrode creates a capacitance (C3) between the sense electrode and the shield layer. This C3 component causes a relatively slow-response sensitivity contribution to the total effective capacitance (Cs) (FIG. 3).

Figure 4:
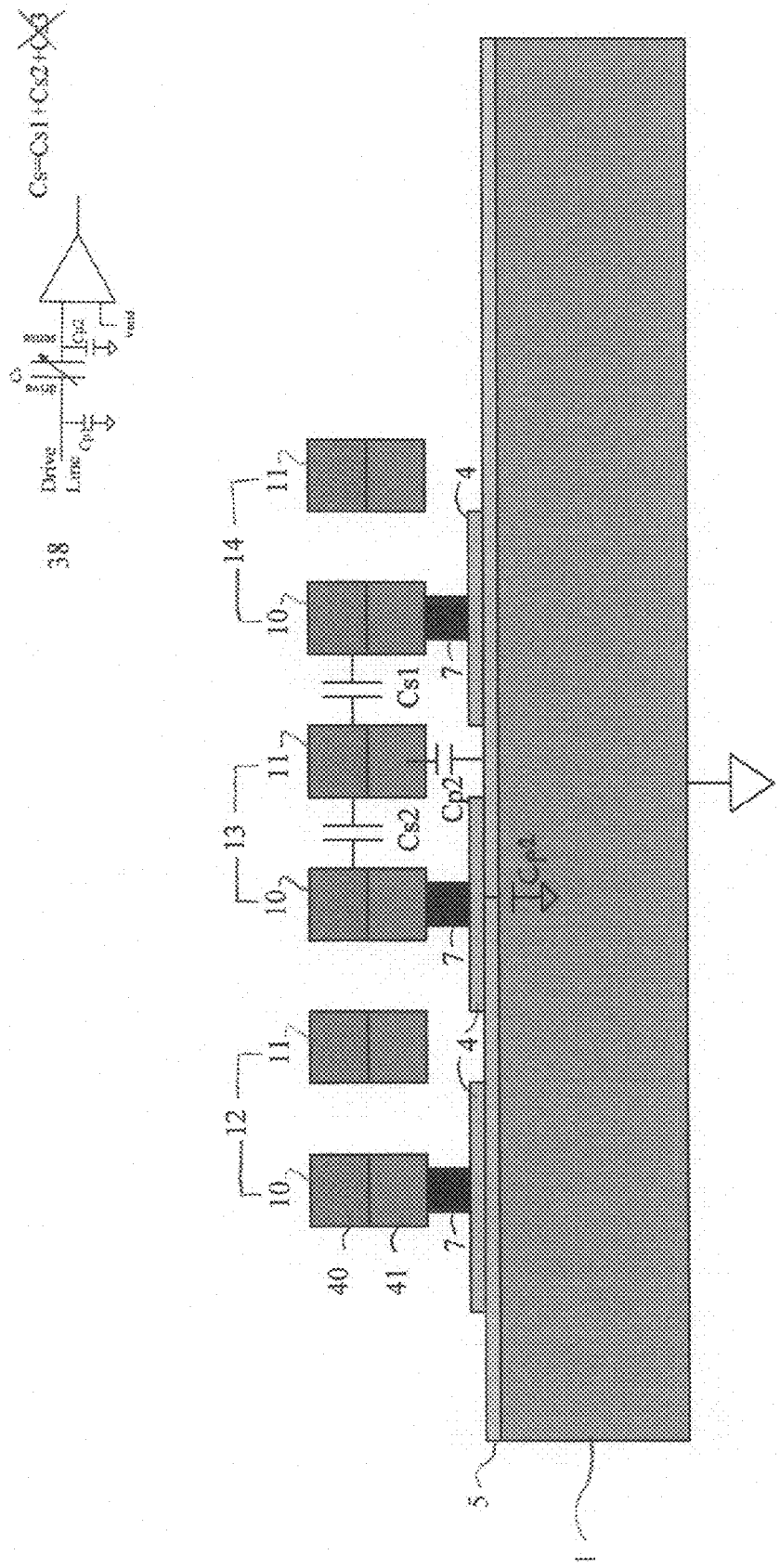
FIG. 4 depicts a preferred embodiment wherein the drive electrode (10) of the sensing electrode pairs (12, 13, and 14) is suspended by a post (7) above an interrupted shield layer (4) disposed on top of an insulating layer deposited on the substrate (1). The sense electrodes (each 11) are suspended above an area of the substrate that lacks shielding. The inset shows a circuit (38) illustrating this embodiment, wherein the total sensing capacitance (Cs) is the sum of sensing capacitances Cs1 and Cs2. Parasitic capacitances Cp1 and Cp2 are also illustrated. Chemical sensing material is not shown in this illustration. In the embodiment depicted, each electrode is shown as being comprised of two layers (40 and 41).

Avoiding the placement of shield layer material below the sense electrode may eliminate this C3 capacitance. As seen in FIG. 4, C3 is replaced by a parasitic capacitance (Cp2) created between the sense electrode and the substrate. Cp2 does not affect Cs and the elimination of C3 reduces Cs, but that reduction in amplitude is offset by the more rapid response obtained without C3. As long as the shield layer extends to the edges of the sense line, as shown in FIG. 4 (the width of the gap in the shield layer is equal to the width of the sense electrode), the reduction in Cs1 and Cs2 that results from such a configuration is small.

The chemical sensing material utilized in the sensing electrode pair of the present invention may be any sorbent material capable of adsorbing or absorbing a target analyte from the ambient environment in which chemical detection is desired.[1] Sorption can be chemisorption or physisorption, and in either case causes an electrical, chemical, or physical change in the sensing material. The term "target analyte" as used herein includes any organic or inorganic molecules, including complex biolmolecules, such as proteins and protein complexes, lipids, nucleic acids, and oligonucleotides, as well as any other molecular species desired to be sensed by sensor. The chemical sensing material can be in solid or liquid form and may be composed of conductive, semiconductive, or electrically insulating materials. It may be made to adhere to the electrode pair or upon the uppermost surface of the substrate or both. The chemical sensing material can be synthesized directly between or directly on the electrode pair or deposited on the electrodes or the substrate after synthesis. Preferably, the chemical sensing material adheres to the electrodes of the electrode pair(s) with which it is associated, and does not substantially degrade the materials used to form the electrode or other parts of the sensor array. Additionally, the chemical sensing material is sufficiently stable to function for the duration required.

Accordingly, the choice of chemical sensing material to use will depend upon the target analyte one desires to detect with the sensing electrode pair. Those of skill in the art are aware of which materials are capable of absorbing different chemicals, and it is thus left to the artisan's discretion. In general, classes of materials that may be employed as chemical sensing materials include, but are not limited to: polymers, porphyrins, and other structured materials; carbon nanotubes; functionalized solgels; xerogels; zeolites; ceramics; epoxies; functionalized gold nanospheres; polymer composites (mixtures of polymers and other materials); biomolecules, such as antibodies, antigens, receptors, cells, lipoproteins; and ionic liquids; ion exchange resins. A listing of preferred materials appears below:

TABLE 1

Representative analyte/sensor material combinations

| Analyte | Sensitive material |
|---|---|
| Nerve agent (e.g., Sarin, Soman) | Fluoroalcohol containing polymer (e.g., siloxane fluoroalcohol |
| Alcohol | Hydroxyl or acetate containing polymer (e.g., polyvinyl acetate or polyvinyl alcohol) |
| Fuels | Polyisobutylene, polydimethyl siloxane, polyethylene vinyl acetate |
| Carbon Dioxide, Nitrogen Dioxide, Sulfur Dioxide | Porphyrins, amine-containing solgels, metal oxides (e.g., tin oxide, tungsten oxide) |

In a preferred embodiment, the chemical sensing material is selected from 29H,31H-Phthalocyanine, 98%; 5,10,15,20-Tetra-p-tolyl-21H,23H-porphine; 5,10,15,20-Tetraphenyl-21H,23H-porphine cobalt(II); 5,10,15,20-Tetraphenyl-21H, 23H-porphine; 5,10,15,20-Tetraphenyl-21H,23H-porphine copper (II); Tetrakis(4-cumylpenoxyl)-phthalocyanine, 97%; 5,10,15,20-Tetra(4-pyridyl)-21H,23H-porphine; 5,10,15,20-Tetraphenyl-21H,23H-porphine nickel(II); 5,10,15,20-Tetraphenyl-21H,23H-porphine iron(III) chloride; 5,10,15,20-Tetraphenyl-21H,23H-porphine zinc; Acrylonitrile/ Butadiene/Styrene Resin; Alginic Acid, Sodium Salt (Algin); Butyl Methacrylate/Isobutyl Methacrylate Copolymer (50/50 Copolymer); Ethylene/Acrylic Acid Copolymer (Acrylic Acid content 15%); Ethylene/Ethyl Acrylate Copolymer (Ethyl Acrylate content 18%); Poly(vinyl N-octadecylcarbamate); Poly(vinyl stearate) Mw~90,000; Poly(vinyl cinnamate) Mw~200,000; Poly(ethylene co-vinyl acetate) 40% vinyl acetate; Poly(ethylene co-vinyl acetate) 18% vinyl acetate; Poly(ethylene co-vinyl acetate) 25% vinyl acetate; Ethylene/Vinyl Acetate (Vinyl Acetate content 14%); Ethylene/Vinyl Acetate (Vinyl Acetate content 9%); Poly(ethylene oxide); Polyethylenimine High Mw; Siloxanefluoroalcohol; Poly(9-vinylcarbazole); Polyurethane; Polyepichlorohydrin; Poly(dimethylsiloxane) 1,000 cSt; Poly(dimethylsiloxane) 100,000 cSt; Ethylene/Propylene (Ethylene content 60%); Polyethylene; Poly(vinyl alcohol) 87-89% hydrolized Mw 31,000-50,000; Hydroxylpropyl cellulose Mw 60,000; Ethyl cellulose Ethoxyl content 50%; Hydroxylpropyl methyl cellulose (10% Hydroxylpropyl and 30% Methoxyl); Polyisobutylene Mw 1350; Cyanopropyl methyl—Di methyl silicone; Phenylmethyl silicone; Cyanopropyl methyl Phenylmethyl silicone; Phenylmethyl diphenyl silicone; Dicyanoalkyl silicone; Polyether Urethane; Polycarbonate Urethane; Siloxane; Poly(dimethylsiloxane) 100,000 cSt and Polyethylenimine High Mw; Siloxane, high acetate content; Epo-Tek 390 Polyimide; Epo-Tek 600-4 Polyimide; or Epo-Tek 1011 Base Polyimide.

The chemical sensing material used in the sensing electrode pair of this invention must be in electrical communication with the electrode pair. The term "electrical communication," as used herein, refers to a relationship such that changes in the chemical sensing material due to the adsorption or binding of a chemical will cause a change in at least one electrical parameter of the sensing electrode pair when electrical power is supplied to the pair. As stated above, electrical communication may be established by placing the chemical sensing agent on the electrode pair or the substrate through coating or other deposition methods, or direct synthesis on the electrode and/or on the substrate surface.

A chemical sensing material used in the sensing electrode pair of this invention may interact with (i.e., by adsorbtion (a surface effect) or absorption (a bulk effect) or bind one or a plurality of different chemicals. Moreover, the adsorption or absorption of a one or more target analytes to a chemical sensing material may result in different quantitative and/or qualitative effect on the electrical parameters of the electrode pair when electrically powered.

The target analytes to which the chemical sensing agent utilized in this invention are responsive is almost limitless. As long as one can identify a chemical sensing agent that binds to, adsorbs, absorbs, or otherwise interacts with a target analyte to produce a detectable change in an electrical property of the sensing electrode pair, that target analyte can be detected using a sensor according to the invention. Classes of target analytes that can be detected by the sensing electrode pair of this invention include, but are not limited to: chemical warfare agents (nerve gas, such as soman, sarin, mustard gas, etc.) and molecules that are considered simulants for such compounds; explosives (e.g., TNT, nitro-compounds, etc.) and explosives simulants; common solvents and volatile organic compounds (toluene, benzene, trichloroethylene, chloroform, acetone, ethanol, methanol, etc.); emission gases ($CO_2$, CO, $NO_2$, NO, SO, $SO_2$, etc.); polycyclic hydrocarbons; and biological molecules (peptides, lipids, sugars, nucleotides, polynucleotides, proteins, antibodies, whole cells, virus particles, bacterial cells, fungi).

The table below lists some of the chemicals that have been detected with chemical sensing agents and the lowest concentration of detectability observed.

TABLE 2

| Class | Chemical | LDC* (ppm) | Chemical | LDC* (ppm) |
|---|---|---|---|---|
| Chemical Warfare Agents | HD | 0.97 | GB | 0.07 |
| | GA | 0.0072 | GD | 0.0063 |
| CWA Simulants | CEE | 1 | DMMP | 0.18 |
| | DIMP | 0.1 | | |
| Volatile Organic Compounds | Acetone | 11 | Isopropyl Alcohol | 84 |
| | Acetonitrile | 25 | Methyl Alcohol | 21 |
| | Benzene | 142 | Octane | 49 |
| | Bromobenzene | 7 | Tetrahydrofuran | 7 |
| | Ethyl acetate | 37 | Toluene | 61 |
| | Ethyl alcohol | 63 | | |
| Nitro-compounds | Nitrobenzene | 0.02 | Nitropropane | 5 |
| | Nitrotoluene | 0.001 | | |
| Other | CO2 | 10 | Humidity | 1% |

*Note: the Lowest Detected Concentrations (LDC) were achieved without analyte pre-concentration in a laboratory controlled flow system in dry conditions, ppm = parts per million

TABLE 3

| Analyte | Polymer Used |
|---|---|
| Industrial solvents | |
| Acetone | SXFA |
| Acetonitrile | SXFA |
| Benzene | OV225 |
| Bromobenzene | SXFA |
| Ethyl acetate | SXFA |
| Ethyl alcohol | SXFA |
| Isopropyl Alcohol | SXFA |
| Methyl Alcohol | SXFA |
| Octane | OV225 |
| Tetrahydrofuran (THF) | SXFA |
| Toluene | OV225 |
| Chemical warfare agent simulants | |
| Chloroethylether (CEE) | PECH, PEVA, SXFA, OV275 |
| Diisopropyl methylphosphonate (DIMP) | SXFA |
| Dimethyl-methylphosphonate (DMMP) | SXFA |
| Explosives byproducts and impurities | |
| Nitrobenzene | SXFA, OV275 |
| Nitropropane | SXFA |
| Nitrotoluene | SXFA |

According to one embodiment, the sensing electrode pair is calibrated before use in a test environment. The calibration is preferably performed with a gas, vapor, or liquid mixture wherein the concentration of one of the target analytes is varied. During the calibration, one or more chosen electrical parameter values versus the varying concentration of the analyte is obtained. Such calibration data is preferably obtained for all analytes to be detected by the electrode pair (or by the plurality of electrode pairs if present in a chemical sensor of this invention). In the event that only complex data is available, pattern-matching software (e.g., neural networks) can be utilized to correlate the response of the device to each specific analyte.

The synthesis of the various components of the electrode pair of this invention may be achieved by a variety of different techniques well-known in the art. Preferably the techniques utilize standard microelectronics and MEMS processing methods. These include, but are not limited to spin coating, dip coating, powder pressing, tape casting, screen printing, curtain deposition, physical sputtering, reactive sputtering, physical vapor deposition, chemical vapor deposition, ion beam, e-beam deposition, molecular beam epitaxy, laser deposition, plasma deposition, electrophoretic deposition, magnetophoretic deposition, thermophoretic deposition, stamping, centrifugal casting, gel casting, extrusion, electrochemical deposition, screen and stencil printing, brush painting, or a combination of one or more of such methods.

In a preferred embodiment, the components are arranged by the steps of: depositing the substrate; depositing or creating the masked or patterned shield layer; depositing a masked or patterned support post; depositing, growing or creating a masked or patterned electrode layer; and depositing the chemical sensitive coating. For example, a coating comprising a polymeric chemical sensing material may be applied using an inkjet head similar to that used in an ink jet printer. The head, which is mounted on a translation stage, has a 30 or 80 μm diameter nozzle that expels droplets of a polymer solution. Each drop is typically a few tens of picoliters in volume and 30-100 μm in diameter.

According to another embodiment, the invention provides a chemical sensor comprising a sensing electrode pair, as described above, and circuitry electrically connected to the electrode pair, wherein the circuitry can detect a change in an electrical parameter of the sensing electrode pair. The term "electrical parameter," as used herein, refers to any or a combination of detectable electrical parameters, including resistance, capacitance, inductance, impedance, phase angle, loss factor, dissipation, breakdown voltage, electrical temperature coefficient of an electrical property, Nernst current, impedance associated with ion conducting, open circuit potential, as well as an electrochemical property, an electronic property, a magnetic property, a thermal property, a mechanical property, or an optical property that can be detected or measured. Preferably, an electrical parameter is selected from capacitance, current, resistance, or voltage. Most preferably, the parameter is conductance.

In all cases, this invention requires that the material compositions used for all elements of the sensing electrode pair and associated circuitry in the chemical sensor maintain their physically integrity in the presence of all species of analytes in the environment of use for a duration equal to or greater than the desired life for the sensor. In some instances, it may be desirable to utilize at least copies of the same electrode pair in a chemical sensor because, in the event that one such electrode pair fails, the redundant electrode pair provides the necessary signal for reliable operation of the sensor.

In a preferred embodiment, the chemical sensor further includes a power source operatively connected to the electrode pair. That energy source may also provide power to the shield layer, if present in the sensing electrode pair. Any suitable power source can be used. Depending on application, different power sources may be used. Suitable energy sources include batteries, as well as electrical energy provided from a hardwired source (e.g., a generator, an electrical power grid, etc.).

Figure 5:
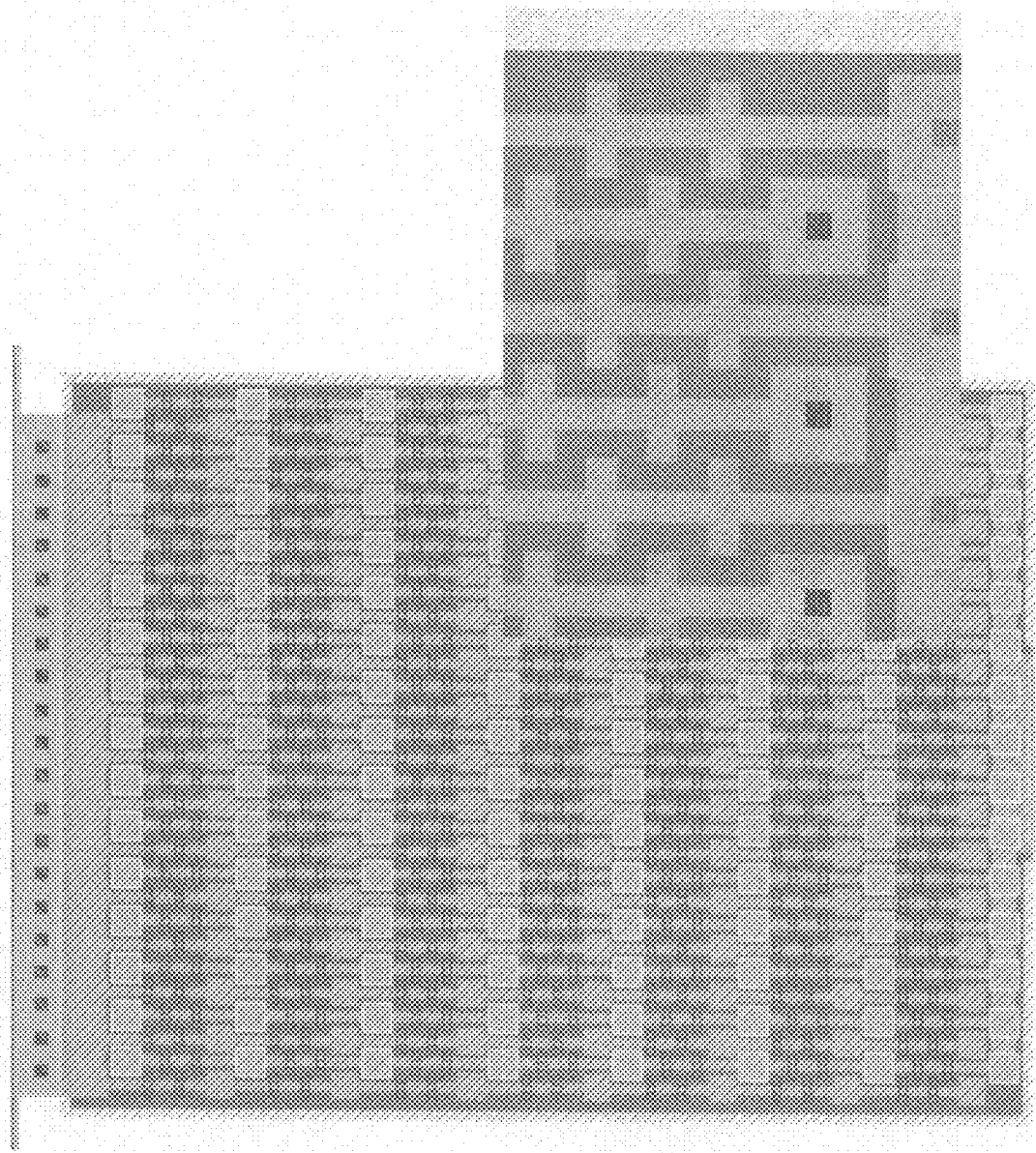
FIG. 5, panel A, depicts a top-down view of an interdigitated sensor array (50) according to the invention that comprises 15 drive (52) and sense (54) electrode pairs (each 56) suspended above a substrate (1) on top of which has been disposed a shield layer (4). Suspension of the electrodes above the substrate is accomplished by spaced anchors (not shown) positioned beneath anchor engaging elements (58). In this embodiment, each electrode is also shown to contain lateral extensions (60) to further increase surface area available for coating with chemical sensing material (not shown). Connectors (62 and 64) are shown for electrically connecting the drive and sense electrodes of each electrode pair to other sensor components. Panel B is an enlargement of the lower right corner of the illustration in panel A. Here, the drive and sense electrodes (52 and 54) are designated "d" and "s", respectively. In panel B of this Figure, as in FIGS. 6 and 7, the gold area designates the substrate (1), the thin blue borderline (5) designates an insulating layer (5) between the substrate (1) layer and the brown shield layer (4). Also, the area shaded red indicates that a chemical sensing layer, or plurality of different chemical sensing layers, has been applied to the chip. In panel B, the purple shaded structures are electrodes, and black designates an anchor (7).

In a more preferred embodiment, the chemical sensor of this invention comprises a plurality sensing electrode pairs. Even more preferred is a chemical sensor wherein the chemical sensing material of at least one of the plurality of sensing electrode pairs differs from the chemical sensing material of another of the plurality of sensing electrode pairs. In one of the most preferred embodiments (illustrated in FIGS. 5-7), the chemical sensor comprises at least 15 pairs of sensing electrodes, wherein each pair comprises a chemical sensing material that differs from the chemical sensing material of each of the other pairs.

In another highly preferred embodiment, the chemical sensor of the present invention comprises a plurality of elevated sensing electrode pairs arrayed on a chip (e.g., a silicon wafer) in accordance with the invention. The chip also comprises electrical connections for both the drive and the sense electrodes of each electrode pair. Preferably, each of the sense electrodes and each of the drive electrodes share a common connection to a power source.

Such arrays of sensing electrode pairs are particularly well-suited to scaled-up production and are typically fabricated using integrated circuit (IC) design technologies. For example, the plurality of sensing electrode pairs and the electrically connected circuitry that can detect a change in an electrical parameter of the sensing electrode pairs can easily be integrated onto the front end of a simple amplifier and interfaced to an A/D converter. This will efficiently feed the data stream from the sensing electrode pairs directly into a neural network software or hardware analysis section. Microfabrication techniques can integrate the electrode pairs directly onto a microchip that also contains the circuitry for analog signal conditioning/processing and then data analysis.

In another embodiment, the invention provides a method of detecting a target analyte comprising the steps of exposing a chemical sensor of the present invention to an environment suspected of comprising the target analyte; and detecting the presence or absence of said target analyte.

In yet another aspect, the invention provides a method of manufacturing a microchip comprising a chemical sensor according to the invention.

Although the invention has been described with reference to the above examples, it will be understood that modifications and variations are encompassed within the spirit and scope of the invention. Accordingly, the invention is limited only by the appended claims.

All of the compositions and methods described and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference in their entirety to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A sensing electrode pair, comprising:
   a. a substrate;
   b. a pair of spaced sensing electrodes elevated above the substrate, wherein one of the electrodes of the electrode pair is a drive electrode and the other electrode of the electrode pair is a sense electrode in electrical communication with the drive electrode, and wherein each of the drive electrode and sense electrode is elevated above the substrate by at least one post disposed between the substrate and the electrode so as to space the electrode from an upper surface of the substrate;
   c. a shield layer disposed on the upper surface of the substrate and underlying the post(s) elevating the electrodes; and
   d. a chemical sensing material disposed on at least a portion of at least one of the drive electrode and sense electrode of the electrode pair, wherein the chemical sensing material is responsive to a target analyte.

2. A sensing electrode pair according to claim 1, wherein the substrate comprises an inert material.

3. A sensing electrode pair according to claim 1, wherein the chemical sensing material is applied as a substantially uniform layer on the drive and sense electrodes.

4. A sensing electrode pair according to claim 1, wherein at least one of the drive electrode and sense electrode is elevated above the substrate by a plurality of posts.

5. A sensing electrode pair according to claim 1, wherein the chemical sensing material is responsive to a plurality of target analytes.

6. A chemical sensor, comprising:
   a. a sensing electrode pair according to claim 1; and
   b. circuitry in electrical communication with the electrodes of the sensing electrode pair, wherein the circuitry can detect a change in an electrical parameter of the sensing electrode pair.

7. A chemical sensor according to claim 6 further comprising a power supply for energizing the sensing electrode pair operatively connected thereto.

8. A chemical sensor according to claim 6, wherein the electrical parameter is selected from the group consisting of capacitance, current, resistance, and voltage.

9. A chemical sensor according to claim 6 comprising a plurality sensing electrode pairs, each according to claim 1.

10. A chemical sensor according to claim 9, wherein the chemical sensing material disposed on least one of the sensing electrode pairs differs from the chemical sensing material disposed on another of the sensing electrode pairs.

11. A chemical sensor according to claim 10, wherein the plurality of sensing electrode pairs are arrayed on a microchip that further comprises electrical connections for both the drive electrodes and the sense electrodes of each electrode pair.

12. A method of sensing a target analyte in a fluid, comprising positioning a chemical sensor according to claim 6 in an environment and using the chemical sensor to determine whether the environment contains the target analyte.

13. A method according to claim 12 wherein the fluid is selected from the group consisting of a vapor, a gas, and a liquid.

14. A method according to claim 12 wherein the target analyte is selected from the group consisting of a volatile organic chemical and a biological material.

15. A method according to claim 12 wherein the chemical sensor is configured to detect a plurality of a different target analyte species.

16. A method of making a sensing electrode pair according to claim 1, comprising using microfabrication techniques to build the posts and electrodes.

* * * * *